(12) United States Patent
Wernle et al.

(10) Patent No.: US 12,714,568 B2
(45) Date of Patent: Aug. 25, 2026

(54) ADDITIVELY MANUFACTURED IMPLANT WITH CERAMIC COATING

(71) Applicant: Zimmer, Inc., Warsaw, IN (US)

(72) Inventors: James D. Wernle, Warsaw, IN (US); Steven Conrad, Albion, IN (US); William Paul Rodgers, III, Warsaw, IN (US); Tayler Kreider, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 869 days.

(21) Appl. No.: 17/973,999

(22) Filed: Oct. 26, 2022

(65) Prior Publication Data

US 2023/0137797 A1 May 4, 2023

Related U.S. Application Data

(60) Provisional application No. 63/273,653, filed on Oct. 29, 2021.

(51) Int. Cl.

| | |
|---|---|
| ***A61F 2/30*** | (2006.01) |
| ***B22F 10/14*** | (2021.01) |
| ***B33Y 40/20*** | (2020.01) |
| ***B33Y 80/00*** | (2015.01) |
| ***C23C 4/11*** | (2016.01) |
| ***C23C 4/134*** | (2016.01) |
| *B33Y 10/00* | (2015.01) |

(52) U.S. Cl.
CPC .......... *A61F 2/30907* (2013.01); *B33Y 40/20* (2020.01); *B33Y 80/00* (2014.12);
(Continued)

(58) Field of Classification Search
CPC . A61F 2002/30973; A61F 2002/30907; B33Y 40/20; B33Y 80/00
See application file for complete search history.

(56) References Cited

U.S. PATENT DOCUMENTS 5,716,414 A 2/1998 Caldarise
5,897,592 A * 4/1999 Caldarise .............. B33Y 10/00 623/901

(Continued)

FOREIGN PATENT DOCUMENTS

EP 3269333 A1 1/2018
EP 3845204 A1 7/2021

(Continued)

OTHER PUBLICATIONS

"European Application Serial No. 22204129.5, Communication Pursuant to Article 94(3) EPC mailed Feb. 20, 2025", 7 pgs.

(Continued)

*Primary Examiner* — Marcia L Watkins
(74) *Attorney, Agent, or Firm* — Schwegman Lundberg & Woessner, P.A.

(57) ABSTRACT

An implant can be implantable into a human body and can include a metallic substrate and a ceramic layer. The metallic substrate can be formed by additive manufacturing. The metallic substrate can be engageable with a bone. The metallic substrate can include an inner surface, an outer surface, and a plurality of retention features. The inner surface can define a plurality of pores configured to promote bone ingrowth into the metallic substrate. The plurality of retention features can include a proximal portion connected to the outer surface and the proximal portion can define a proximal width. The ceramic layer can be a bearing surface that can be spray coated to the metallic substrate and formed around the retention features to interlock the ceramic layer with the metallic substrate.

10 Claims, 5 Drawing Sheets

(52) U.S. Cl.
CPC ............... *A61F 2002/30383* (2013.01); *A61F 2002/30968* (2013.01); *A61F 2002/30985* (2013.01); *A61F 2310/00023* (2013.01); *A61F 2310/00604* (2013.01); *A61F 2310/00616* (2013.01); *B22F 10/14* (2021.01); *B22F 2301/205* (2013.01); *B33Y 10/00* (2014.12); *C23C 4/11* (2016.01); *C23C 4/134* (2016.01)

(56) References Cited

U.S. PATENT DOCUMENTS

| | | | | |
|---|---|---|---|---|
| 2007/0208427 | A1* | 9/2007 | Davidson | A61F 2/30767 623/23.51 |
| 2023/0404764 | A1* | 12/2023 | Salito | A61F 2/30767 |

FOREIGN PATENT DOCUMENTS

| | | | |
|---|---|---|---|
| FR | 2626766 | A1 | 8/1989 |
| WO | WO-2020190251 | A1 | 9/2020 |

OTHER PUBLICATIONS

"European Application Serial No. 22204129.5, Extended European Search Report mailed Feb. 20, 2023", 10 pgs.

"European Application Serial No. 22204129.5, Response filed Jun. 16, 2025 to Communication Pursuant to Article 94(3) EPC mailed Feb. 20, 2025", 18 pgs.

"European Application Serial No. 22204129.5, Response filed Oct. 9, 2023 to Extended European Search Report mailed Feb. 20, 2023", 27 pgs.

* cited by examiner

ADDITIVELY MANUFACTURED IMPLANT WITH CERAMIC COATING

CLAIM OF PRIORITY

This patent application claims the benefit of priority, under 35 U.S.C. Section 119(e), to James D. Wernle, U.S. Patent Application Ser. No. 63/273,653, entitled "ADDITIVELY MANUFACTURED IMPLANT WITH CERAMIC COATING," filed on Oct. 29, 2021, which is hereby incorporated by reference herein in its entirety.

BACKGROUND

This application relates generally, though not by way of limitation to three dimensional (3D) printing or additive manufacturing. 3D printing is a process whereby liquid, powder, or another base materials is used to form, often layer-by-layer, a three-dimensional structure using various machines (often referred to as 3D printers). To print a 3D object using a 3D printer, a CAD (computer-aided design) file is often converted to printing information that is transferred to a 3D printer, which uses the printing information to create the 3D object. In some examples of 3D printing, metals can be used to print complex shapes.

BRIEF DESCRIPTION OF THE DRAWINGS

In the drawings, which are not necessarily drawn to scale, like numerals may describe similar components in different views. Like numerals having different letter suffixes (or prefixes) may represent different instances of similar components. The drawings illustrate generally, by way of example, but not by way of limitation, various embodiments discussed in the present document.

FIG. S illustrates a schematic view of a method.

Figure 9:
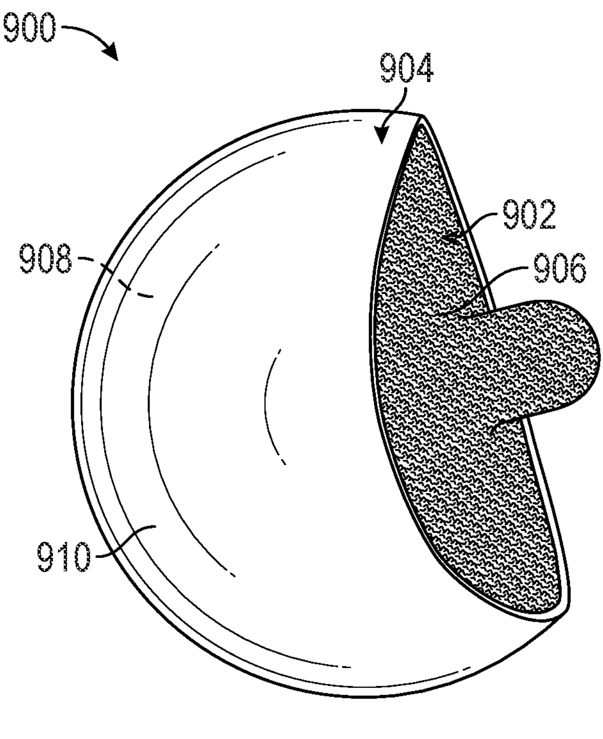

FIG. 9 illustrates an isometric view of an implant.

Figure 10:
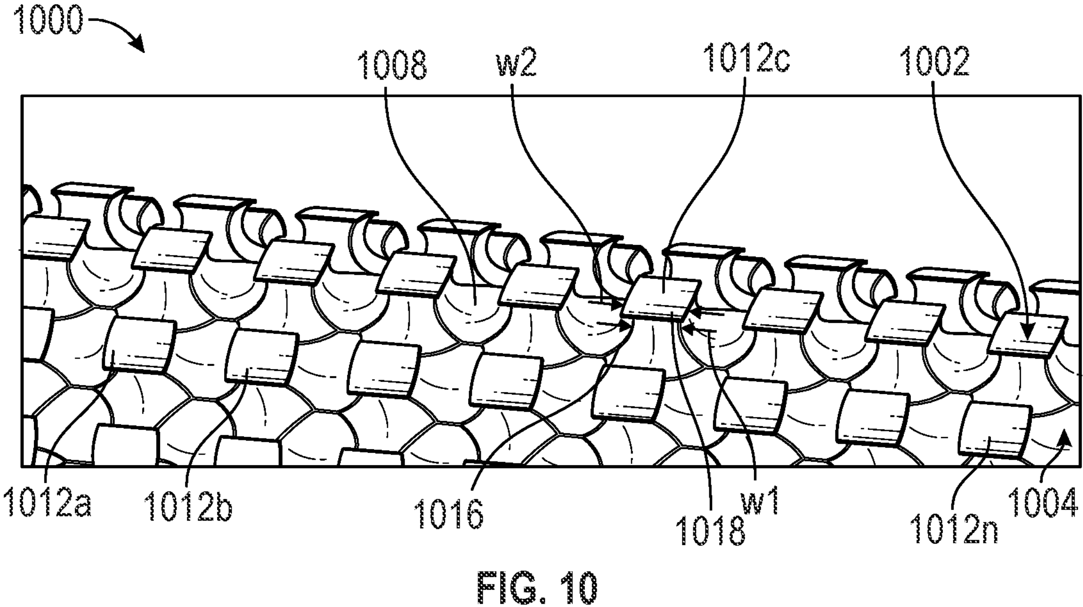

FIG. 10 illustrates an enlarged isometric view of an implant.

DETAILED DESCRIPTION

Ceramic coatings are desirable for use in implants because they can provide a very smooth surface that can create a relatively low friction interface that can help improve component life. However, ceramics by themselves may be incapable of withstanding typical forces experienced by joint implants. Ceramic-metallic composite coatings can help to address this issue; however, such coatings may require a substrate to have a rough surface to ensure adhesion of the coating to the substrate. Also, 3D printing of implant substrates can be relatively time-consuming and therefore expensive.

This disclosure helps to address these issues by using a binder jet 3D printing method that can produce a naturally rough surface for receipt of a ceramic plasma spray coating. The binder jet substrate can also be relatively fast and therefore cost effective. Further, because the binder jet can use relatively small metallic particles during printing, the substrate can be printed to include interlocking components on the surface of the substrate. The interlocking components can receive the ceramic plasma spray coating and can help further adhere the ceramic layer to the substrate to help improve component strength and durability.

The above discussion is intended to provide an overview of subject matter of the present patent application. It is not intended to provide an exclusive or exhaustive explanation of the invention. The description below is included to provide further information about the present patent application.

Figures 1, 2A, 2B:
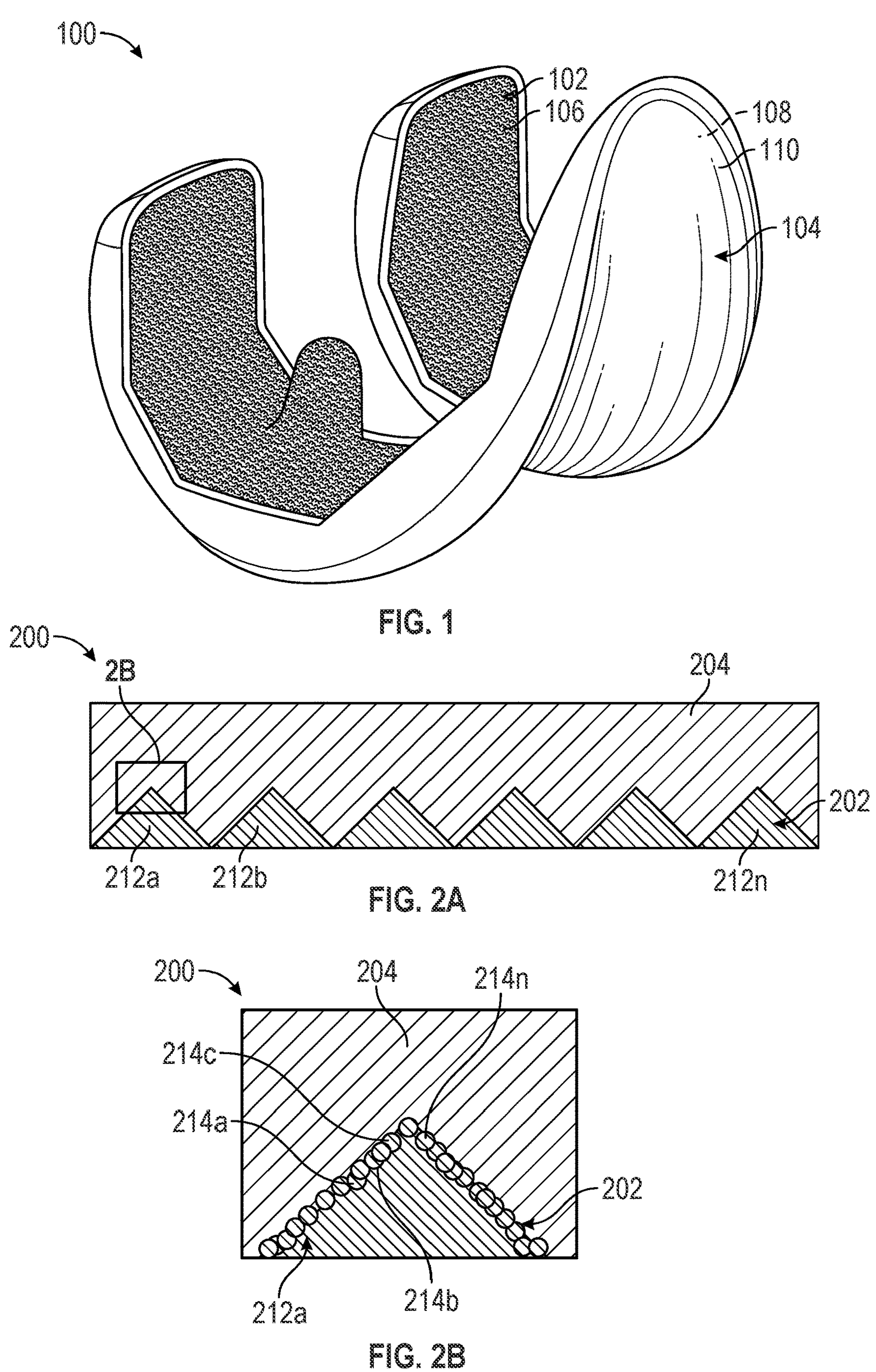
FIG. 1 illustrates an isometric view of an implant.
FIG. 2A illustrates an enlarged cross-sectional view of an implant.
FIG. 2B illustrates an enlarged cross-sectional view of an implant.

FIG. 1 illustrates an isometric view of an implant 100 that is implantable into a human body. The implant 100 can be a distal femoral implant, such as a condyle replacement. The implant 100 can optionally be other types of implants, such as a femoral head implant, a single femoral condyle implant, a tibial bearing implant, a humeral head implant, or a glenoid implant.

The implant 100 can include a substrate 102 and an outer layer 104. The substrate 102 can be a metallic substrate formed by additive manufacturing, such as a porous titanium substrate. The substrate 102 can include an inner surface 106 that can be engageable with a bone and an outer surface 108 that can be bonded to the outer layer 104. The inner surface 106 can define a plurality of pores configured to promote bone ingrowth into the substrate 102. As discussed in further detail below, the outer surface 108 can include one or more retention features.

The outer layer 104 can be a ceramic layer applied or adhered to the substrate 102. For example, the outer layer 104 can be a plasma spray coating applied to the substrate 102. The outer layer 104 can be formed around the retention features (as discussed in further detail below) to interlock (or secure or connect) the outer layer 104 with or to the substrate 102. Following curing or drying of the outer layer 104, the outer layer 104 can form a bearing surface 110 of the implant 100. As shown in FIG. 1, the outer layer 104 can be applied to front (anterior) portions, side (medial or lateral) portions, rear (posterior) portions, upper (superior), or lower (inferior) portions of the substrate 102. The outer layer 104 can be a composite of titanium dioxide and aluminum oxide, but can be other composite or non-composite ceramic materials.

FIG. 2A illustrates an enlarged cross-sectional view of an implant 200. FIG. 2B illustrates a further enlarged cross-sectional view of the implant 200. FIGS. 2A and 2B are discussed together below. The implant 200 can be similar to the implant 100 discussed above; FIGS. 2A and 2B show how the implant 200 can include retention features formed from additive manufacturing, such as binder jetting. Any of the implants discussed above or below can be modified to include retention features.

As shown in FIG. 2A, the implant 200 can include a substrate 202 and a coating or outer layer 204. The coating 204 can be a ceramic composite (the same or similar to the coating 104) and the substrate 202 can be a binder jet printed substrate (the same or similar to the substrate 102). Only a portion of the substrate 202 is shown in FIGS. 2A and 2B. FIG. 2A shows that the substrate 202 can include retention features 212*a*-212*n*. The retention features 212 can have various shapes or can be a similar, repeating shape. As shown in FIG. 2A, the shape of the retention features 212 can be triangles. The retention features 212 can form a relatively rough surface of the substrate 202 for the coating or outer layer 204 to bind or adhere to.

As shown in FIG. 213, the retention features 212 can each be formed of many particles 214, which can be assembled (such as through binder jetting) to form the retention features. The particles 214*a*-214*n* can be cured and densified following the binder jetting. The particles 214 can be printed in various other shapes as discussed in further detail below.

Figure 3:
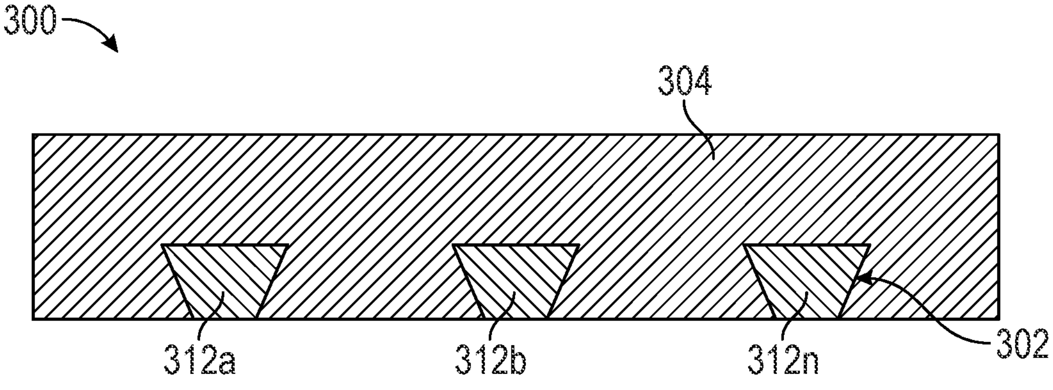
FIG. 3 illustrates an enlarged cross-sectional view of an implant.

FIG. 3 illustrates an enlarged cross-sectional view of an implant 300. The implant 300 can be similar to the implants 100 and 200, in that the implant 300 can include a substrate 302 and an outer coating 304 that can be similar to the substrates and outer coatings, respectively, discussed above. The implant 300 can differ in that the shape of the retention features 312*a*-312*n* can be a trapezoid or a keystone, Optionally, the shape of the retention features 312*a*-312*n* can be a trapezoidal prism or a partial trapezoidal prism. Such a shape can help to interlock or secure the outer coating 304 to the substrate 302, as discussed in further detail below with respect to FIG. 5. Optionally, the retention features 312*a*-312*n* can have other shapes such as a rectangular prism or a cuboid.

Figure 4:
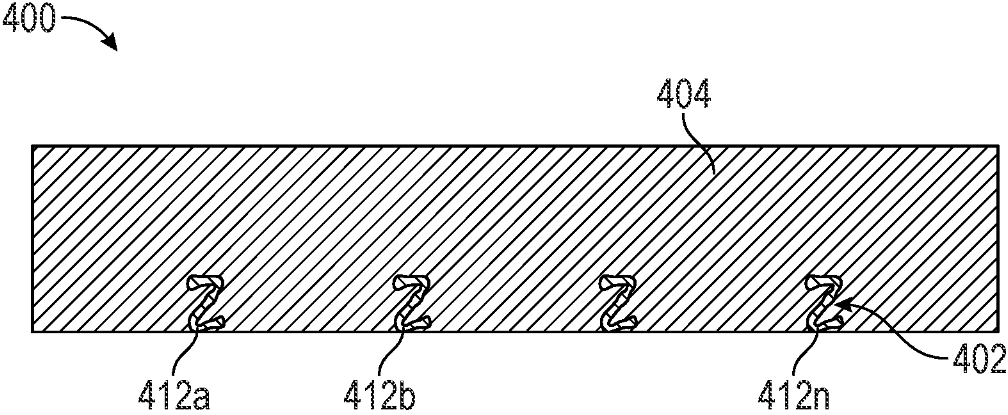
FIG. 4 illustrates an enlarged cross-sectional view of an implant.

FIG. 4 illustrates an enlarged cross-sectional view of an implant 400. The implant 400 can be similar to the implants 100-300, in that the implant 400 can include a substrate 402 and an outer coating 404 that can be similar to the substrates and outer coatings, respectively, discussed above. The implant 400 can differ in that the shape of retention features 412*a*-412*n* can have a cross-sectional Z-shape. That is, the retention features 412*a*-412*n* can have a depth in addition to the shown height and width.

Figure 5:
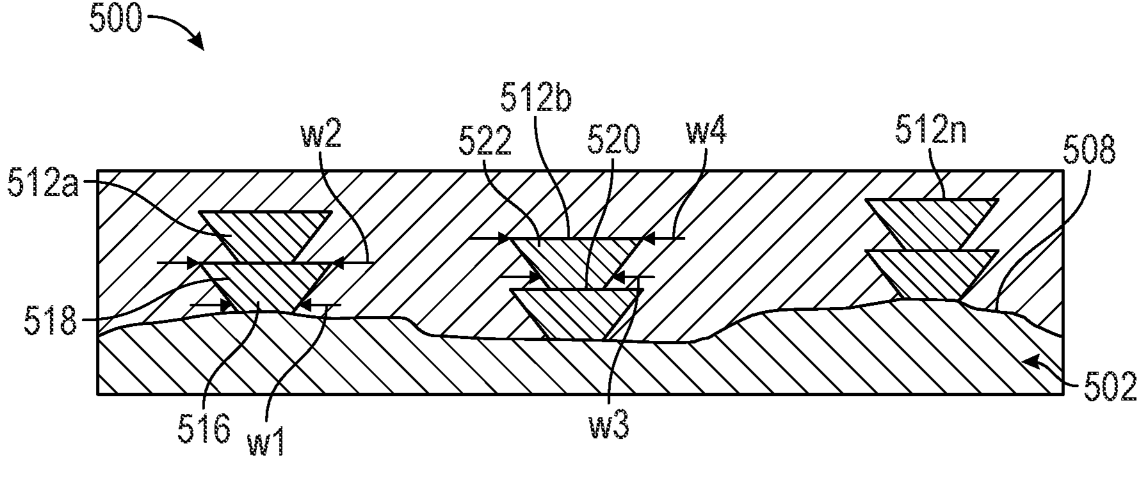
FIG. 5 illustrates an enlarged cross-sectional view of an implant.

FIG. 5 illustrates an enlarged cross-sectional view of an implant 500. The implant 500 can be similar to the implants 100-400, in that the implant 500 can include a substrate 502 and an outer coating 504 that can be similar to the substrates and outer coatings, respectively, discussed above. The implant 500 can differ in shape of retention features 512*a*-512*n* can be a keystone shape including multiple projections.

For example, the retention feature 512*a* can include a proximal portion 516 connected to an outer surface 508 of the substrate 502. The proximal portion 516 defining a proximal width w1. The retention feature 512*a* can also include a distal portion 518 connected to the proximal portion 516. The distal portion 518 can define a distal width w2 that is larger than the proximal width. Because the distal portion 518 of the retention feature 512*a* is relatively larger or wider, it increases a force required to separate the outer coating 504 from the substrate 502. The retention features of the implants 100-400 discussed above and 600-700 discussed below can include such width variations to help reduce a chance of delamination or separation of the spray coated outer layer (e.g., 504) from the substrate e.g., 502).

Additionally, the retention features can include multiple width variations. For example, the retention feature 512*b* can include the widths w1 and w2 and can also include a medial portion 520 defining a width w3 and can include an outer distal portion 522 defining a width w4 where the width w4 can be larger than the width w3. These width variations in the retention features 512 can further help to limit separation or delamination of the outer coating 504 from the substrate 502, such as during use of the implant 500.

Figure 6:
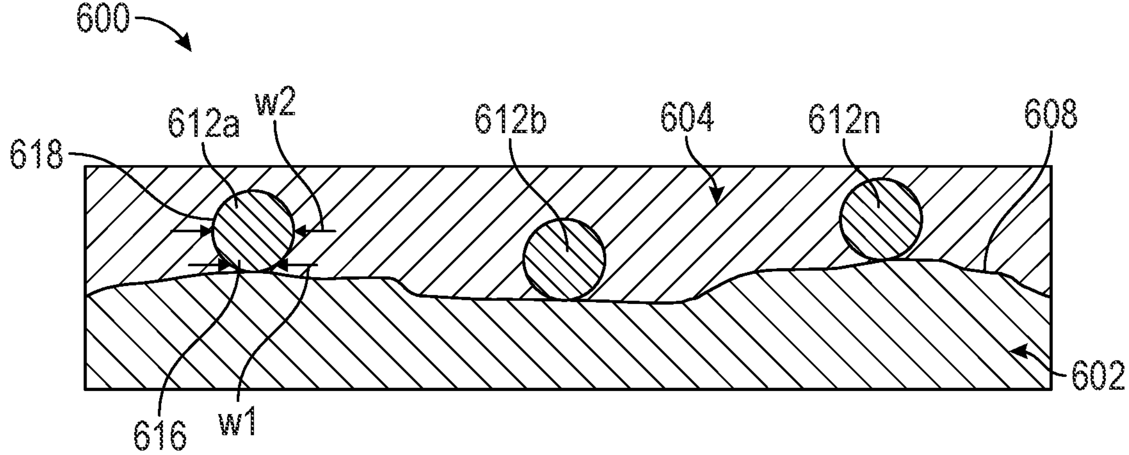
FIG. 6 illustrates an enlarged cross-sectional view of an implant.

The width w4 can also be larger than the width w1 and can also be larger than the width w2. The widths w1 and w3 can be the same as can the widths w2 and w4. Alternatively, the widths w1-w4 can be different. Also, optionally, the retention features 512 can all have widths that are consistent between retention features. Alternatively, the retention features 512 can have widths that vary between retention features. Optionally, the retention features 512 can be located (or can be located in higher density) on a rounded portion of the substrate 502, such as to help secure the outer coating 504 to the substrate 502 where separation may normally occur, FIG. 6 illustrates an enlarged cross-sectional view of an implant 600. The implant 600 can be similar to the implants 100-500, in that the implant 600 can include a substrate 602 and an outer coating 604 that can be similar to the substrates and outer coatings, respectively, discussed above. The implant 600 can differ in that the shape of retention features 612*a*-612*n* can have a cross-sectional circular shape or a partial circle shape. Optionally, the retention features 612*a*-612*n* can have a spherical shape or a partial spherical shape. In either case, the retention features 612 can include proximal portion 616 defining a width w1 and can include a distal portion 618 defining a width w2 that is larger or wider than the width w1 to help limit separation of the outer coating 604 from the substrate 602, such as during use of the implant 600. The proximal portion 616 can be connected to an outer surface 608 of the substrate 602.

Figure 7:
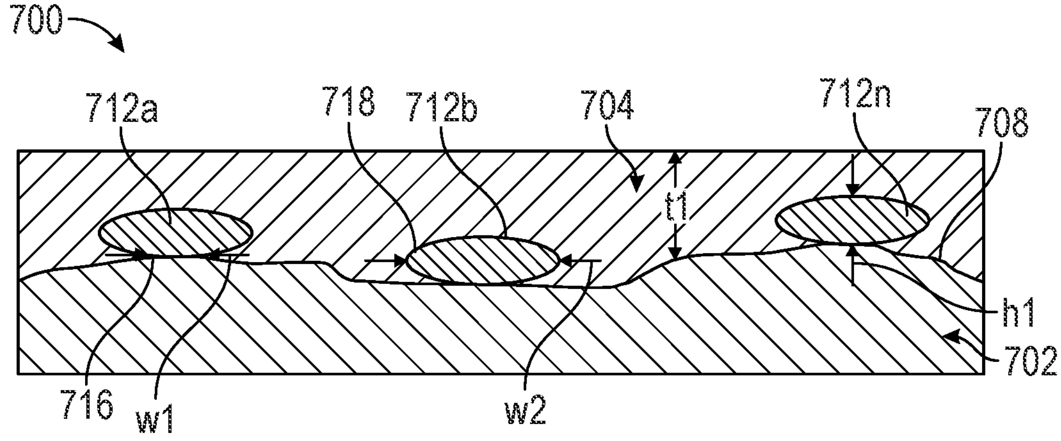
FIG. 7 illustrates an enlarged cross-sectional view of an implant.

FIG. 7 illustrates an enlarged cross-sectional view of an implant 700. The implant 700 can be similar to the implants 100-600, in that the implant 700 can include a substrate 702 and an outer coating 704 that can be similar to the substrates and outer coatings, respectively, discussed above. The implant 700 can differ in shape of retention features 712*a*-712*n* can have a cross-sectional oval shape or a partial oval shape. Optionally, the retention features 712*a*-712*n* can have a ovoid shape or a partial ovoid shape. In either case, the retention features 712 can include proximal portion 716 defining a width 16 and can include a distal portion 718 defining a width w2 that is larger or wider than the width w1 to help limit separation of the outer coating 704 from the substrate 702, such as during use of the implant 700.

FIG. 7 also shows that the outer coating 704 can define or have a thickness t1. The thickness t1 can optionally vary to match a contour of the outer surface 708. The thickness t1 can be between 100 and 300 micrometers (micron). The thickness t1 can optionally be about 200 micrometers.

FIG. 7 also shows that the retention features 712 can define or have a height h1. The height h1 can be between 10 micrometers and 100 micrometers, which means that the retention features 712 can extend from an outer surface 708 by 10 micrometers to 100 micrometers. The height h1 can optionally be between 20 micrometers and 50 micrometers. In some examples, the thickness t1 can be increased to accommodate the height h1 of the retention feature 712. Also, the thickness t1 can be varied around other portions of the implant 700. For example, edges of the implant 700 can have a reduced thickness and bearing surfaces (e.g., condyle replacement surfaces) can have a relatively larger thickness.

Because the binder jetting process can use relatively small particulates, as discussed above with respect to FIGS. 2A and 2B, the retention features (such as the retention features 212 or 712) can be made at a relatively small scale, such as between 20 micrometers and 50 micrometers. This can allow the ceramic coating (e.g., outer layer 704) to be applied in a relatively thin layer (having a relatively small thickness) on top of the substrate (e.g., the substrate 702), while allowing for the use of interlocking features and still minimizing the impact to the outer layer or coating by the interlocking features. That is, the interlocking features can be large enough to increase interlocking between the substrate and the outer layer, but small enough to minimize impact on the profile (e.g., smoothness) of the outer layer.

Figure 8:
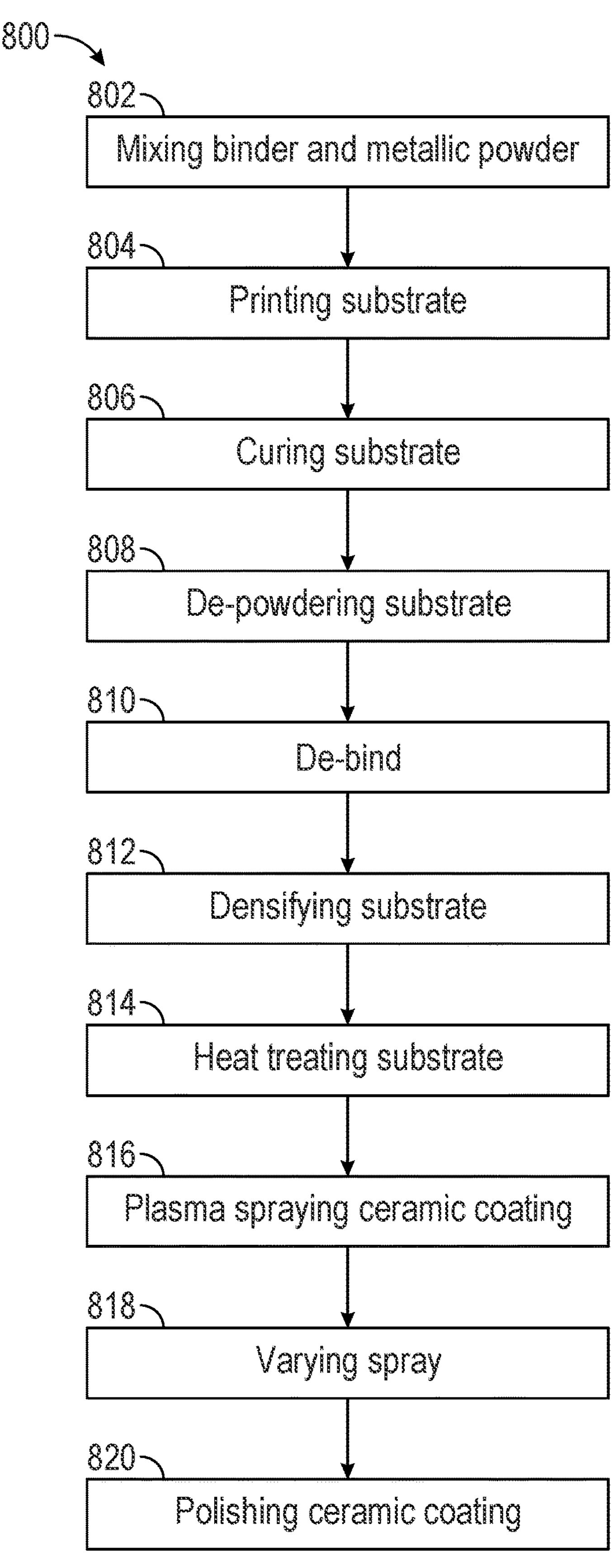

FIG. 8 illustrates a schematic view of the method 800, in accordance with at least one example of this disclosure. The method 800 can be a method of manufacturing an implant using additive manufacturing and plasma spray coating. More specific examples of the method 800 are discussed below. The steps or operations of the method 800 are illustrated in a particular order for convenience and clarity; any of the discussed operations can be performed in a different sequence, simultaneously, in series, or in parallel without materially impacting other operations. The method 800 as discussed includes operations performed by multiple different actors, devices, and/or systems. It is understood that subsets of the operations discussed in the method 800 can be attributable to a single actor, device, or system could be considered a separate standalone process or method.

The method 800 can begin at step 802 where a binder and metallic powder can be mixed. Optionally, other components can be added to the mix either before or after mixing the binder and the metallic powder. The binder can be a temperature activated adhesive and the metallic powder can be titanium. At step 804, the metallic powder and binder mixture can be printed into a preliminary metallic substrate, such as using a binder jetting process. An outer surface of the preliminary metallic substrate can include a plurality of retention features on an outer surface of the preliminary metallic substrate. For example, the outer surface 508 of the implant 500 can include retention features 512.

At step 806, the preliminary metallic substrate can be cured, such as through a heating process to cross link the substrate. At step 808, the preliminary metallic substrate can be de-powdered such that excess powder can be removed from the preliminary metallic substrate. At step 810, the preliminary metallic substrate cab be de-binded such that the binder can be released from the preliminary metallic substrate. At step 812, the preliminary metallic substrate can be densified, such as by sintering the preliminary metallic substrate to form a hardened metallic substrate. The preliminary metallic substrate can be densified in other ways. Sintering can be performed using one or more of heat or pressure applied to the preliminary metallic substrate. Optionally steps 810 and 812 can be performed together or at the same time.

At step 814, the hardened or densified metallic substrate can be heat treated, such as one or more of annealing, normalizing, hardening, tempering, aging, quenching, or the like. Optionally, the hardened or densified metallic substrate can be further densified such as through hot isostatic pressing (HIP). At step 816, a ceramic coating can be plasma sprayed on the outer surface and the retention features of the hardened metallic substrate to interlock the ceramic coating to the hardened metallic substrate.

At step 818, the outer surface can be polished of the ceramic coating to form a bearing surface of the implant. Optionally, a spray angle of a plasma sprayer can be varied during plasma spraying the ceramic coating on the hardened metallic substrate. At step 820, a spray thickness of the ceramic coating can be varied on the hardened metallic substrate.

FIG. 9 illustrates an isometric view of an implant 900 that is implantable into a human body. The implant 900 can be similar to the implants 100-700 discussed above; the implant 900 can differ in that the implant 900 can be a humeral head implant. The implant 900 can optionally be other types of implants, such as a femoral oral head implant.

The implant 900 can include a substrate 902 and an outer layer 904. The substrate 902 can be formed by additive manufacturing, such as binder jetting. The substrate 902 can be a metallic substrate porous titanium substrate. The substrate 902 can include an inner surface 906 that can be engageable with a bone and can be porous to help promote bone ingrowth. The inner surface 906 can define a plurality of pores configured to promote bone ingrowth into the substrate 902. The outer surface 908 can be a relative rough surface configured to be bonded to the outer layer 904. The outer surface 908 can include one or more retention features, such as those discussed above, Once bonded to the outer surface, the outer layer 904 can form a bearing surface 910 of the implant 900, engageable with a glenoid or glenoid implant, for example.

FIG. 10 illustrates an enlarged cross-sectional view of an implant 1000. The implant 100 can be similar to the implants discussed above, in that the implant 1000 can include a substrate 1002 and an outer coating 1004 that can be similar to the substrates and outer coatings, respectively, discussed above. The implant 1000 can differ in that the shape of retention features 1012*a*-1012*n* can be a complex or irregular shape.

For example, the retention feature 1012*c* can include a proximal portion 1016 connected to an outer surface 1008 of the substrate 1002. The proximal portion 1016 can define a proximal width w1. The retention feature 1012*c* can also include a distal portion 1018 connected to the proximal portion 1016. The distal portion 1018 can define a distal width w2 that is larger than the proximal width w1. Because the distal portion 1018 of the retention feature 1012*a* is relatively larger or wider, it can increase a force required to separate the outer coating 1004 from the substrate 1002. The retention features of the implants discussed above and below can include such width variations to help reduce a chance of delamination or separation of the spray coated outer layer (e.g., 1004) from the substrate (e.g., 1002).

Additionally, the retention features 1012 can include multiple shape variations. For example, the proximal portion 1016 can form a tapered or curved rectangular pyramid shape or square pyramid shape connected to the distal portion 1018, such that the smallest width (w1) of the proximal portion 1016 is located near the largest width (w2) of the distal portion 1018. These shape variations in the retention features 1012 can further help to limit separation or delamination of the outer coating 1004 from the substrate 1002, such as during use of the implant 1000.

Also, the distal portion 1018 can have a relatively square or rectangular shape (or rectangular prism shape with a relatively small height), which can help to increase a surface area of the distal portion 1018 and can add multiple edges and vertices to the retention features 1012. These geometric features of the retention features 1012 can help to further increase a force required to separate or delaminate the outer coating 1004 from the substrate 1002, such as during use of the implant 1000 following implantation.

Optionally, the retention features 1012 can be located (or can be located in higher density) on a rounded portion of the substrate 1002, such as to help secure the outer coating 1004 to the substrate 1002 where separation may be more likely to occur.

NOTES AND EXAMPLES

The following, non-limiting examples, detail certain aspects of the present subject matter to solve the challenges and provide the benefits discussed herein, among others.

Example 1 is an implant implantable into a human body, the implant comprising: a metallic substrate formed by additive manufacturing, the metallic substrate engageable with a bone, the metallic substrate including: an inner surface defining a plurality of pores configured to promote bone ingrowth into the metallic substrate; an outer surface; and a plurality of retention features, each including: a proximal portion connected to the outer surface, the proximal portion defining a proximal width; and a distal portion connected to the proximal portion, the distal portion defining a distal width larger than the proximal width; and a ceramic layer spray coated to the metallic substrate and formed around the retention features to interlock the ceramic layer with the metallic substrate, the ceramic layer forming a bearing surface of the implant.

In Example 2, the subject matter of Example 1 optionally includes wherein the metallic substrate is a porous titanium substrate formed from binder jet additive manufacturing.

In Example 3, the subject matter of Example 2 optionally includes wherein the ceramic layer is spray coated to the porous titanium substrate using plasma spray coating.

In Example 4, the subject matter of any one or more of Examples 2-3 optionally include wherein the ceramic layer is made of a composite of titanium dioxide and aluminum oxide.

In Example 5, the subject matter of any one or more of Examples 1-4 optionally include wherein the retention feature has a cross sectional shape of a keystone, a trapezoid, a partial circle, or a partial oval.

In Example 6, the subject matter of any one or more of Examples 1-5 optionally include wherein the ceramic layer has a thickness between 100 and 300 micrometers.

In Example 7, the subject matter of Example 6 optionally includes wherein the retention feature extends from the outer surface between 10 micrometers and 100 micrometers.

In Example 8, the subject matter of any one or more of Examples 6-7 optionally include wherein the retention feature extends from the outer surface between 20 micrometers and 50 micrometers.

In Example 9, the subject matter of any one or more of Examples 1-8 optionally include wherein the retention featured is located on a rounded portion of the metallic substrate.

In Example 10, the subject matter of any one or more of Examples 1-9 optionally include wherein the implant is a femoral head implant, a femoral condyle implant, a tibial bearing implant, a humeral head implant, or a glenoid implant.

Example 11 is a method of manufacturing an implant, the method comprising: printing a metallic powder and binder mixture into a preliminary metallic substrate, an outer surface of the preliminary metallic substrate including a plurality of retention features on an outer surface of the preliminary metallic substrate; curing the preliminary metallic substrate through a heating process; de-powdering the preliminary metallic substrate; densifying the preliminary metallic substrate by sintering the preliminary metallic substrate to form a hardened metallic substrate; heat, treating the hardened metallic substrate; plasma spraying a ceramic coating on the outer surface and the retention features of the hardened metallic substrate to interlock the ceramic coating to the hardened metallic substrate.

In Example 12, the subject matter of Example 11 optionally includes polishing an outer surface of the ceramic coating to form a bearing surface of the implant.

In Example 13, the subject matter of any one or more of Examples 11-12 optionally include varying a spray angle of a plasma sprayer during plasma spraying the ceramic coating on the hardened metallic substrate.

In Example 14, the subject matter of any one or more of Examples 11-13 optionally include varying a spray thickness of the ceramic coating on the hardened metallic substrate.

In Example 15, the subject matter of any one or more of Examples 11-14 optionally include wherein the ceramic coating has a thickness between 100 and 300 micrometers.

In Example 16, the subject matter of any one or more of Examples 11-15 optionally include wherein the retention feature extends from the outer surface between 20 micrometers and 50 micrometers.

In Example 17, the subject matter of any one or more of Examples 11-16 optionally include wherein the metallic substrate is a porous titanium substrate formed from binder jet additive manufacturing.

In Example 18, the subject matter of Example 17 optionally includes wherein the ceramic coating comprises a composite of titanium dioxide and aluminum oxide.

Example 19 is an implant implantable into a human body, the implant comprising: a metallic substrate formed by additive manufacturing, the metallic substrate engageable with a bone, the metallic substrate including: an inner surface defining a plurality of pores configured to promote bone ingrowth into the metallic substrate; an outer surface; and a plurality of retention features; and a ceramic layer spray coated to the metallic substrate and formed around the retention features to interlock the ceramic layer with the metallic substrate, the ceramic layer forming a bearing surface of the implant.

In Example 20, the subject matter of Example 19 optionally includes wherein the metallic substrate is a porous titanium substrate formed from binder jet additive manufacturing, wherein the ceramic layer is spray coated to the porous titanium substrate using plasma spray coating, and wherein the ceramic layer is made of a composite of titanium dioxide and aluminum oxide.

In Example 21, the subject matter of Example 1 optionally includes wherein the proximal portion has a shape of a curved pyramid.

In Example 22, the subject matter of Example 1 optionally includes wherein the distal portion has a shape of a rectangular prism.

In Example 23, the apparatuses or method of any one or any combination of Examples 1-22 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the tennis "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An implant implantable into a human body, the implant comprising:

a metallic substrate formed by additive manufacturing, the metallic substrate engageable with a bone, the metallic substrate including:

an inner surface defining a plurality of pores configured to promote bone ingrowth into the metallic substrate;

an outer surface; and a plurality of retention features extending from a rounded portion of the metallic substrate, each of the plurality of retention features including:

a proximal portion connected to the outer surface, the proximal portion defining a proximal width; and a distal portion connected to the proximal portion, the distal portion defining a distal width larger than the proximal width; and a ceramic layer spray coated to the metallic substrate and formed around the retention features to interlock the ceramic layer with the metallic substrate, the ceramic layer forming a bearing surface of the implant, the ceramic layer including a thickness between 100 and 300 micrometers.

2. The implant of claim 1, wherein the metallic substrate is a porous titanium substrate formed from binder jet additive manufacturing.

3. The implant of claim 2, wherein the ceramic layer is spray coated to the porous titanium substrate using plasma spray coating.

4. The implant of claim 2, wherein the ceramic layer is made of a composite of titanium dioxide and aluminum oxide.

5. The implant of claim 1, wherein the retention feature extends from the outer surface between 10 micrometers and 100 micrometers.

6. The implant of claim 1, wherein the retention feature extends from the outer surface between 20 micrometers and 50 micrometers.

7. The implant of claim 1, wherein the implant is a femoral head implant, a femoral condyle implant, a tibial bearing implant, a humeral head implant, or a glenoid implant.

8. An implant implantable into a human body, the implant comprising:

a metallic substrate formed by additive manufacturing, the metallic substrate engageable with a bone, the metallic substrate including:

an inner surface defining a plurality of pores configured to promote bone ingrowth into the metallic substrate;

an outer surface; and a plurality of retention features; and a ceramic layer spray coated to the metallic substrate and formed around the retention features to interlock the ceramic layer with the metallic substrate, the ceramic layer forming a bearing surface of the implant, and the ceramic layer having a thickness between 100 and 300 micrometers.

9. The implant of claim 8, wherein the metallic substrate is a porous titanium substrate formed from binder jet additive manufacturing, wherein the ceramic layer is spray coated to the porous titanium substrate using plasma spray coating, and wherein the ceramic layer is made of a composite of titanium dioxide and aluminum oxide.

10. The implant of claim 8, wherein the plurality of retention features are located on a rounded portion of the metallic substrate.

* * * * *